United States Patent [19]
Bjornvad et al.

[11] Patent Number: 6,043,075
[45] Date of Patent: Mar. 28, 2000

[54] ENDOGLUCANASE

[75] Inventors: Mads Eskelund Bjornvad, Frederiksberg; Martin Schulein, Copenhagen; Iben Angelica Norrevang, Hillerod, all of Denmark

[73] Assignee: Novo Nordisk A/S, Bagsvaerd, Denmark

[21] Appl. No.: 08/995,280

[22] Filed: Dec. 19, 1997

[30] Foreign Application Priority Data

Dec. 20, 1996 [DK] Denmark .................................. 1483/96

[51] Int. Cl.$^7$ .............................. C12N 9/42; C12N 9/00; C12N 9/24; C07H 21/04
[52] U.S. Cl. .......................... 435/209; 435/183; 435/189; 435/200; 435/201; 435/202; 435/206; 435/207; 435/208; 435/210; 435/212; 435/219; 435/252.33; 536/23.2
[58] Field of Search ...................... 435/183, 189, 435/200, 201, 202, 206, 207, 208, 209, 210, 212, 219, 193, 232; 536/23.2

[56] References Cited

U.S. PATENT DOCUMENTS 5,275,944  1/1994  Himmel et al. .......................... 435/209

FOREIGN PATENT DOCUMENTS 0 511 933 A2  11/1992  European Pat. Off. .
0 511 933 A3  11/1992  European Pat. Off. .

OTHER PUBLICATIONS

Ratto et al., "Application of Thermostable Xylanase of Dictyoglomus sp. In Enzymatic Treatment of Kraft Pulps", Appl. Microbiol. Biotechnol (1994) 41:130–133.

Hudson et al., "The Cellulase Activity of an Extreme Thermophile", Appl. Microbiol Biotechnol (1991) 35:270–273.

Honda et al., "Isolation of a New Cellulase Gene From a Thermophilic Anaerobe and its Expression In *Escherichia Coli*", Appl. Microbiol. Biotechnol. (1988) 29:264–268.

Hiroyuki Honda et al., "Cloning and Expression in *Escherichia Coli* of a Thermoanaerobacter Cellulolyticus Gene Coding For Heat–Stable β–Glucanase", Appl. Microbiol. Biotechnol (1987) 25: pp. 480–483.

Bonnie L. Maidak et al., "The Ribosomal Database Project", 1994 Oxford University Press, Nucleic Acids Research, 1994, vol. 22, No. 17, pp. 3485–3487.

*Primary Examiner*—Rebecca E. Prouty
*Assistant Examiner*—Elizabeth Slobodyansky
*Attorney, Agent, or Firm*—Steve T. Zelson; Valeta Gregg

[57] ABSTRACT

An endoglucanase obtainable from Dictyoglomus exhibiting optimum activity at a temperature above 85° C. is disclosed.

11 Claims, No Drawings

ENDOGLUCANASE

CROSS-REFERENCE TO RELATED APPLICATIONS

This application claims priority under 35 U.S.C. 119 of Danish application no. 1483/96 filed Dec. 20, 1996, the contents of which are fully incorporated herein by reference.

FIELD OF INVENTION

The present invention relates to an enzyme with cellulolytic activity at high temperature, especially an endoglucanase; a cloned DNA sequence encoding the enzyme with cellulolytic activity; a method for providing a gene encoding such an enzyme; a method of producing the enzyme; an enzyme composition comprising the enzyme with cellulolytic activity; and the use of said enzyme and enzyme composition for a number of industrial applications.

BACKGROUND OF THE INVENTION

Cellulases or cellulolytic enzymes are enzymes involved in hydrolysis of cellulose. In the hydrolysis of native cellulose, it is known that there are three major types of cellulase enzymes involved, namely cellobiohydrolase (1,4-beta-D-glucan cellobiohydrolase, EC 3.2.1.91), endo-beta-1,4-glucanase (endo-1,4-beta-D-glucan 4-glucanohydrolase, EC 3.2.1.4) and beta-glucosidase (EC 3.2.1.21).

Especially the endoglucanases (EC No. 3.2.1.4) constitute an interesting group of hydrolases for the mentioned industrial uses. Endoglucanases catalyses endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucano hydrolase, but the abbreviated term endoglucanase is used in the present specification. Reference can be made to T.-M. Enveri, "Microbial Cellulases" in W. M. Fogarty, Microbial Enzymes and Biotechnology, Applied Science Publishers, p. 183–224 (1983); Methods in Enzymology, (1988) Vol. 160, p. 200–391 (edited by Wood, W. A. and Kellogg, S. T.); Béguin, P., "Molecular Biology of Cellulose Degradation", Annu. Rev. Microbiol. (1990), Vol. 44, pp. 219–248; Béguin, P. and Aubert, J-P., "The biological degradation of cellulose", FEMS Microbiology Reviews 13 (1994) p.25–58; Henrissat, B., "Cellulases and their interaction with cellulose", Cellulose (1994), Vol. 1, pp. 169–196.

Cellulases are synthesized by a large number of microorganisms which include fungi, actinomycetes, myxobacteria and true bacteria but also by plants. Especially endoglucanases of a wide variety of specificities have been identified. Many bacterial endoglucanases have been described (Henrissat, B. and Bairoch, A. (1993) Biochem J. 293:781–788; Gilbert, H. J. and Hazlewood, G. P. (1993) J. Gen. Microbiol. 139:187–194).

The Clostridia subdivision is a very diverse group of anaerobic bacteria comprising physiologically very different genera. Previously, Clostridium was considered one genus including all endo spore-forming anaerobic bacteria. However the introduction of molecular taxonomic tools such as 16S rDNA sequencing have revealed that the group is heterogenous to a level far above genus. Moreover, various genera of non spore-forming anaerobes were classified within Clostridia, that turned out as a superior taxonomic group, a subdivision. This is in accordance to the highly diversified habitats for these organisms. The subdivision Clostridia, for example, comprises species with optimal growth temperature of a very broad range.

The genus Dictyoglomus comprises extreme thermophilic anaerobic bacteria phylogenetically situated within the Clostridia subdivision. Dictyoglomus spp. are among the most thermophilic organisms within the subdivision Clostridia. In the 16S rDNA phylogenetic tree Dictyoglomus occur with other thermophilic genera such as Thermoanaerobacter, Thermoanaerobacterium and Syntrophomonas as closest relatives. However Dictyoglomus form a deep branch confirming that Dictyoglomus indeed should be considered as a separate genus.

Dictyoglomus sp. strain B1 was isolated from a sludge and pulp sample from a pulpmass cooling tank, i.e. from a manmade thermophilic environment. A xylanase of this organism have been described with respect to temperature optimum (around 90° C.). The xylanase production of this strain have been subjected to studies for fermentation optimization. The presence of endoglucanase from species of the genus Dictyoglomus was never reported. Within the phylum clostridia cellulases have been described from several species of which a few are thermophilic. In few cases the thermostability of endoglucanases have been determined, one of the most studied species is *Clostridium thermocellum* which have proven stable up to 80° C. *Thermoanaerobacter cellulyticus* produces at least two endoglucanases with stability up to 80° C.

Reference can be made to: Hudson et al. (1991) The cellulase activity of an extreme thermophile, Appl. Microbiol. Biotechnol. 35:270–273; Mathrani and Ahring (1991) Isolation and characterization of strictly xylan-degrading Dictyoglomus from man-made thermophilic environment, Arch. Microbiol. 157:13–17; Adamsen et al. (1995) Optimization of extracellular xylanase production by Dictyoglomus sp B1 in continuous-culture, Appl. Microbiol. Biotechnol. 44:327–332; Maidak et al. (1994) The Ribosomal Database Project, Nuc. Acids Res. 22:3485–3487; Honda et al. (1987) Cloning and expression in *E.coli* of a *Thermoanaerobacter cellulyticus* gene encoding for heatstable beta-glucanase, Appl. Microbiol. Biotechnol. 25:480–483; Honda et al. (1988) Isolation of a new cellulase gene from a thermophilic anaerobe and its expression in *E. coli*, Appl. Microbiol. Biotechnol. 29:264–268.

A very important industrial use of cellulolytic enzymes is the use for treatment of cellulosic textile or fabric, e.g. as ingredients in detergent compositions or fabric softener compositions, for bio-polishing of new fabric (garment finishing), and for obtaining a "stone-washed" look of cellulose-containing fabric, especially denim, and several methods for such treatment have been suggested, e.g. in GB-A-1 368 599, EP-A-0 307 564 and EP-A-0 435 876, WO 91/17243, WO 91/10732, WO 91/17244, PCT/DK95/000108 and PCT/DK95/00132. Another important industrial use of cellulytic enzymes is the use for treatment of paper pulp, e.g. for improving the drainage or for deinking of recycled paper.

It is also known that cellulases may or may not have a cellulose binding domain (a CBD). The CBD enhances the binding of the enzyme to a cellulose-containing fiber and increases the efficacy of the catalytic active part of the enzyme.

There is a need for providing economically feasible cellulase enzyme preparations which may be used for applications where cellulase, preferably an endoglucanase, activity at high temperatures is desirable.

The object of the present invention is to provide novel enzyme compositions or recombinant enzymes having substantial cellulolytic activity at high temperature conditions and improved performance in industrial applications, e.g. in paper pulp processing, textile treatment, laundry processes, extraction processes or in animal feed.

SUMMARY OF THE INVENTION

The inventors have now succeeded in cloning and characterizing a DNA sequence from the bacterial genus Dictyoglomus which encodes an enzyme exhibiting cellulolytic activity at extremely high temperatures in a very broad pH range, thereby making it possible to prepare a monocomponent cellulolytic enzyme composition with desired properties.

Accordingly, in a first aspect the invention relates to an enzyme preparation having endoglucanase activity which has optimum activity at a temperature above 85° C., preferably above 90° C., more preferably above 95° C., especially above 100° C.

In its second aspect, the invention relates to an enzyme preparation having endoglucanase activity towards carboxy methyl cellulose (CMC assay) at 70° C. and pH 10 higher than 50%, preferably higher than 55%, more preferably higher than 60%, more preferably higher than 65%, especially higher than 70%, relative to the activity at 70° C. and optimum pH. In its third aspect, the invention relates to a DNA construct comprising a DNA sequence encoding an enzyme having endoglucanase activity and optimum activity above 85° C., preferably above 90° C., more preferably above 100° C., which DNA sequence comprises
  a) the DNA sequence corresponding to the endoglucanase encoding part of the DNA sequence obtainable from the plasmid in *Escherichia coli* DSM 11201, or
  b) an analogue of the DNA sequence corresponding to the endoglucanase encoding part of the DNA sequence obtainable from the plasmid in *Escherichia coli* DSM 11201, which
    i) is homologous, preferably at least 60% homologous, with the DNA sequence corresponding to the endoglucanase encoding part of the DNA sequence obtainable from the plasmid in *Escherichia coli* DSM 11201, or
    ii) hybridizes with the same oligonucleotide probe as the DNA sequence corresponding to the endoglucanase encoding part of the DNA sequence obtainable from the plasmid in *Escherichia coli* DSM 11201, or
    iii) encodes a polypeptide which is homologous, preferably at least 60% homologous, with the polypeptide encoded by a DNA sequence comprising the DNA sequence corresponding to the endoglucanase encoding part of the DNA sequence obtainable from the plasmid in *Escherichia coli* DSM 11201, or
    iv) encodes a polypeptide which is immunologically reactive with an antibody raised against the purified endoglucanase encoded by the DNA sequence corresponding to the endoglucanase encoding part of the DNA sequence obtainable from the plasmid in *Escherichia coli* DSM 11201.

In its fourth, fifth and sixth aspect the invention provides an expression vector harbouring the cloned DNA sequence of the invention, a cell comprising the cloned DNA sequence or the expression vector and a method of producing an enzyme exhibiting cellulolytic activity, which method comprises culturing the cell under conditions permitting the production of the enzyme, and recovering the enzyme from the culture.

In yet another aspect the invention provides an isolated enzyme exhibiting cellulolytic activity, characterized in (i) being free from homologous impurities and (ii) the enzyme is produced by the method described above.

The invention further relates to an isolated enzyme having cellulolytic activity, preferably an endoglucanase, which is encoded by the DNA construct of the invention. Further, the present invention relates to the use of such an enzyme or the enzyme preparation of the invention for industrial applications such as in the textile industry for improving the properties of cellulosic fibres or fabric or for providing a stone-washed look of denim; or in industrial cleaning processes; or in heat extruded polymeric material; or in the conversion of biomass to sugars; or in the production of alcohol; or for predigestion of e.g. grains used in the feed production; or in the production of instant coffee or similar extraction processes.

The invention also relates to an isolated substantially pure biological culture of the *Escherichia coli* strain DSM 11201 harbouring a cellulase encoding DNA sequence, or any mutant of said *E.coli* strain.

DETAILED DESCRIPTION OF THE INVENTION

In the present context, the term "the 20 naturally occuring amino acid residues" denotes the 20 amino acid residues usually found in proteins and conventionally known as alanine (Ala or A), valine (Val or V), leucine (Leu or L), isoleucine (Ile or I), proline (Pro or P), phenylalanine (Phe or F), tryptophan (Trp or W), methionine (Met or M), glycine (Gly or G), serine (Ser or S), threonine (Thr or T), cysteine (Cys or C), tyrosine (Tyr or Y), asparagine (Asn or N), glutamine (Gln or Q), aspartic acid (Asp or D), glutamic acid (Glu or E), lysine (Lys or K), arginine (Arg or R), and histidine (His or H).

The enzyme and the enzyme preparation of the invention is active over a broad pH range, preferably active at a pH between about 4 and about 11, preferably between about 5.5 and about 10.

In a preferred embodiment, the enzyme or the enzyme preparation of the invention is obtainable from or endogeneous to a strain belonging to the phylum Gram Positive Bacteria, more preferably a the strain belonging to the subdivision Clostridia, even more preferably belonging to the genus Dictyoglomus, especially being the species Dictyoglomus sp., DSM 6262.

In the present context the expression "a cloned DNA sequence", either partial or complete, refers to a DNA sequence cloned by standard cloning procedure used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated.

The "cloned DNA sequence" of the invention may alternatively be termed "DNA construct" or "isolated DNA sequence".

The DNA sequence may be of genomic, cDNA, or synthetic origin or any combinations of these.

The cellulase encoding part of the DNA sequence cloned into plasmid pSJ1678 present in *Escherichia coli* DSM 11201 and/or an analogue DNA sequence of the invention may be cloned from a strain of the bacterial genus Dictyoglomus, preferably the strain Dictyoglomus, DSM 6262, producing the enzyme with cellulase, preferably endoglucanase, activity, or another or related organism as described further below.

Alternatively, the analogous sequence may be constructed on the basis of the DNA sequence obtainable from the plasmid present in *Escherichia coli* DSM 11201, e.g be a subsequence thereof, and/or by introduction of nucleotide substitutions which do not give rise to another amino acid sequence of the cellulase encoded by the DNA sequence, but which corresponds to the codon usage of the host organism intended for production of the enzyme, or by introduction of nucleotide substitutions which may give rise to a different amino acid sequence (i.e. a variant of the cellulase of the invention).

When carrying out nucleotide substitutions, amino acid changes are preferably of a minor nature, i.e. conservative amino acid substitutions which do not significantly affect the folding or the enzymatic activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain.

Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al., (1991), Protein Expression and Purification 2, 95–107.

It will be apparent to persons skilled in the art that such substitutions can be made outside the regions critical to the function of the molecule and still result in an active polypeptide. Amino acids essential to the activity of the polypeptide encoded by the cloned DNA sequence of the invention, and therefore preferably not subject to substitution, may be identified according to procedures known in the art, such as site-directed mutagenesis or alanine-scanning mutagenesis (cf. e.g. Cunningham and Wells, (1989), Science 244, 1081–1085). In the latter technique mutations are introduced at every residue in the molecule, and the resultant mutant molecules are tested for biological (i.e. cellulolytic) activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (cf. e.g. de Vos et al., (1992), Science 255, 306–312; Smith et al., (1992), J. Mol. Biol. 224, 899–904; Wlodaver et al., (1992), FEBS Lett. 309, 59–64).

The endoglucanase encoded by the DNA sequence of the DNA construct of the invention may comprise a cellulose binding domain (CBD) existing as an integral part of the encoded enzyme, or a CBD from another origin may be introduced into the endoglucanase thus creating an enzyme hybride. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the endoglucanase and growing the host cell to express the fused gene. Enzyme hybrids may be described by the following formula:

CBD—MR—X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of a polypeptide encoded by the DNA sequence of the invention.

The DNA sequence of the present invention can be cloned from the strain *Escherichia coli* DSM 11201 using standard methods e.g. as described by Sambrook et al., (1989), Molecular Cloning: A Laboratory Manual. Cold Spring Harbor Lab.; Cold Spring Harbor, N.Y.

The DNA sequence of the invention can also be cloned by any general method involving
   cloning, in suitable vectors, a DNA library from any organism, e.g. Dictyoglomus, expected to produce the endoglucanase of interest, transforming suitable host cells with said vectors, culturing the host cells under suitable conditions to express any enzyme of interest encoded by a clone in the DNA library, screening for positive clones by determining any cellulolytic activity of the enzyme produced by such clones, and isolating the enzyme encoding DNA from such clones.

Alternatively, the DNA encoding a cellulase of the invention may, in accordance with well-known procedures, conveniently be cloned from a suitable source, such as any of the below mentioned organisms, by use of synthetic oligonucleotide probes prepared on the basis of the DNA sequence obtainable from the plasmid present in *Escherichia coli* DSM 11201.

Homology of DNA Sequences

The DNA sequence homology referred to above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology, 48, 443–453. Using GAP with the following settings for DNA sequence comparison: GAP creation penalty of 5.0 and GAP extension penalty of 0.3, the (partial) DNA sequence exhibits a degree of identity of at least 60%, preferably of at least 75%, more preferably at least 80%, more preferably at least 90%, more preferably at least 95%, more preferably at least 97% with the DNA sequence corresponding to the endoglucanase encoding part of the DNA sequence obtainable from the plasmid present in *Escherichia coli* DSM 11201.

Hybridization

The hybridization referred to above is intended to indicate that the analogous (partial) DNA sequence hybridizes to an oligonucleotide probe corresponding to the endoglucanase encoding part of the DNA sequence obtainable from the plasmid present in *Escherichia coli* DSM 11201 under certain specified conditions which are described in detail below.

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) Anal. Biochem. 132:6–13), $^{32}$P-dCTP-labeled (specific activity>1×10$^9$ cpm/µg) probe for 12 hours at ca. 45° C. The filter is then washed two times for 30 minutes in 2×SSC, 0.5% SDS at preferably not higher than 55° C., more preferably not higher than 60° C., more preferably not higher than 65° C., even more preferably not higher than 70° C., especially not higher than 75° C.

Molecules to which the oligonucleotide probe hybridizes under these conditions are detected using a x-ray film.

Homology to Amino Acid Sequences

The polypeptide homology referred to above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology, 48, 443–453. Using GAP with the following settings for polypeptide sequence comparison: GAP creation penalty of 3.0 and GAP extension penalty of 0.1, the polypeptide encoded by an analogous (partial) DNA sequence exhibits a degree of identity of at least 60%, preferably of at least 70%, preferably of at least 80%, preferably of at least 85%, more preferably at least 90%, more preferably at least 95%, especially at least 97% with the polypeptide encoded by the endoglucanase encoding part of DNA sequence obtainable from the plasmid present in *Escherichia coli* DSM 11201.

Immunological Cross-reactivity

Antibodies to be used in determining immunological cross-reactivity may be prepared by use of a purified cellulolytic enzyme. More specifically, antiserum against the endoglucanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Microbial Sources

The taxonomy applied below are in accordance with Maidak et al. 1996 (The Ribosomal Database Project. Nucl. Acids Res. 24:82–85).

For the purpose of the present invention the term "obtained from" or "obtainable from" as used herein in connection with a specific source, means that the enzyme is produced or can be produced by the specific source, or by a cell in which a gene from the source has been inserted.

It is at present contemplated that the cellulase of the invention may be obtained from a bacterium, in particular a Gram Positive Bacteria, preferably from the subdivision Clostridia, in particular a strain of the genus Dictyoglomus.

In a preferred embodiment, the cellulase of the invention is obtained from the strain Dictyoglomus, DSM 6262. It is at present contemplated that a DNA sequence encoding an enzyme homologous to the enzyme of the invention may be obtained from other bacterial strains, especially strains belonging to the genus Dictyoglomus.

An isolate of a strain of Dictyoglomus sp. from which a cellulase of the invention can be derived is publicly available from Deutsche Sammlung von Mikroorganismen, DSM 6262.

Further, the plasmid pSJ1678 comprising the DNA sequence encoding the endoglucanase of the invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Oct. 11, 1996 under the deposition number DSM 11201.

Recombinant Expression Vectors

A recombinant vector comprising a DNA construct encoding the enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cells

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells. A preferred host cell includes prokaryotic, archaeal and filamentous fungal cells.

Examples of fungal host cells which, on cultivation, are capable of producing the enzyme of the invention are cells of filamentous fungi such as as strains belonging to any of the genera Aspergillus, Fusarium and Trichoderma, more specifically the strains belonging to the species *Aspergillus niger, Aspergillus oryzae, Fusarium graminerarum* and *Trichoderma reesei.*

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. liquefaciens, B. coagulans, B. circulans, B. lautus, B. megatherium* or *B. thuringiensis*, or strains of Streptomyces, such as *S. lividans* or *S. murinus*, or gram-negative bacteria such as *Escherichia coli*. The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Method of Producing a Cellulolytic Enzyme

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptide" may alternatively be termed "purified polypeptide".

When an expression vector comprising a DNA sequence encoding the enzyme is transformed into a heterologous host cell it is possible to enable heterologous recombinant production of the enzyme of the invention.

Thereby it is possible to make a highly purified or monocomponent cellulolytic composition, characterized in being free from homologous impurities.

In this context homologous impurities means any impurities (e.g. other polypeptides than the enzyme of the invention) which originate from the homologous cell where the enzyme of the invention is originally obtained from.

In the present invention the homologous host cell may be a strain of Dictyoglomus sp.

The medium used to culture the transformed host cells may be any conventional medium suitable for growing the host cells in question. The expressed cellulolytic enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme Compositions

In a still further aspect, the present invention relates to an enzyme composition comprising an enzyme exhibiting cellulolytic activity as described above.

The enzyme composition of the invention may, in addition to the cellulase of the invention, comprise one or more other enzyme types, for instance hemi-cellulase such as xylanase and mannanase, other cellulase or endo-glucanase components, chitinase, lipase, esterase, pectinase, cutinase, phytase, oxidoreductase, protease, or amylase.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Thermostable cellulases have potential uses in a lot of different industries and applications. Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

Uses

In the textile industry cellulases are used for treatment of cotton and other cellulosic materials to obtain a surface treatment of the fibers which result in fabrics with altered properties such as reduced pilling tendency, fuzz removal, softer fabric, better hand or visual effects. Especially cellulases are used to produce a "stone-washed" look of denim. The use of cellulases at high temperatures makes it possible to create new looks of both denim and non denim cotton/cellulosic fabrics. The thermostable cellulases can be included in high temperature treatments of fabric which has not been possible before, cellulase wash over 80° C. or under steam conditions with very low liquor ratio is possible which gives the potential of creating new looks.

Use of thermostable cellulases in industrially cleaning processes makes it possible to make an easier cleaning process when the unwanted material to be removed is based on cellulosic matter. Examples are cleaning of ultra filtration membranes, pipes and the like in food/feed industry.

Incorporation of thermostable cellulase in heat extruded plast and polymer materials with cellulose filler, will result in higher degradeability of these materials in nature.

Lignocellulosic materials make up a big part of agricultural and forestry waste and in paper which is very dominant in municipal waste. This waste is typically burned, which from an energy point of view is an enormous waste of resources. A lot of work has been assigned to the task of developing an effective and economic process for conversion of this biomass to sugars that can be fermented to produce e.g. alcohol for use as fuel. Proposed processes for conversion of lignocellulosics to sugars include the use of cellulases but very high dosages are needed which make them unrealistic in big industrial scale from an economical point of view. The use of thermostable cellulases with liquefying properties makes such a bioconversion process more realistic. Processing at high temperature opens the cell wall structure in a lot of plant materials and makes the cellulose more accessible for enzyme attack.

In the industrial production of alcohol from different kind of grains, the traditional process includes liquefaction with alpha amylase at temperatures around 80–100° C. Inclusion of cellulase in this step will increase the yield of fermentable sugars. This preliquefaction of cellulose will also make the inclusion of traditional cellulases in the following process realistic, due to a higher hydrolysis rate than without preliquefaction.

Predigestion of grains; rye, barley, maize etc for feed production is another potential use of thermostable cellulase, this in order to increase digestibility of the feed in the animal.

Coffee extraction for production of instant coffee is carried out at temperatures 85–150° C. in a battery of percolation columns. Water pass coutercurrent from the most extracted cell to the one just filled with fresh coffee. The operation temperature for the cells with the fresh coffee is approx. 100° C. Inclusion of thermophile cellulases at this point will increase capacity of the columns since the soluble matter is released easier when the cell wall structure is opened.

Inclusion of cellulases in other traditional high temperature processes for extraction of oil or aroma/flavour compounds from natural plant sources will in the same way as for coffee extraction increase capacity or yield. An example is extraction of palm oil or palm kernel oil which is an aqueous high temperature process.

MATERIALS AND METHODS

Deposited Organisms

Dictyoglomus sp. DSM 6262, comprises the cellulase encoding DNA sequence of the invention.

*Escherichia coli* DSM 11201 containing the plasmid comprising the DNA sequence encoding the cellulolytic enzyme of the invention, in the cloning vector pSJ1678.

Other Strains

*E. coli* strain: Cells of *E. coli* SJ2 (Diderichsen, B., Wedsted, U., Hedegaard, L., Jensen, B. R., Sjoholm, C. (1990) Cloning of aldB, which encodes alpha-acetolactate decarboxylase, an exoenzyme from Bacillus brevis. J. Bacteriol., 172, 4315–4321), were prepared for and transformed by electroporation using a Gene Pulser™ electroporator from BIO-RAD as described by the supplier.

Plasmid pSJ1678 as disclosed in the international application published as WO 94/19454 which is hereby incorporated by reference.

General Molecular Biology Methods

DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Isolation of the DNA Sequence Encoding the Cellulytic Enzyme of the Invention

The DNA sequence encoding the endoglucanase of the invention, can be obtained from the deposited organism *E. coli*, DSM 11201, by extraction of plasmid DNA by methods known in the art (Sambrook et al. (1989) Molecular cloning: A laboratory manual, Cold Spring Harbor lab., Cold Spring Harbor, N.Y.).

CLONING OF THE ENDOGLUCANASES GENE

Genomic DNA Preparation

Strain Dictyoglomus sp., DSM 6262, was propagated in a 1 l glass flask for 2 days at 70° C. on the medium as described below.

Composition of the Strict Anaerobic Medium for Strain DSM 6262

1.0 g $NH_4Cl$, 0.1 g NaCl, 0.1 g $MgCl_2$, 0.05 g $CaCl_2$, 0.4 g $K_2HPO_4.3H_2O$, 0.75 g Yeast extract, 4.0 g Beech xylan (Lenzing), 0.5 mg Resazurin, 1.0 ml Trace metals#, 1.0 ml Vitamin solution, 3.0 g $NaHCO_3$, $H_2O$ to 1 l.

Trace metal solution: 2.0 g $FeCl_2.4H_2O$, 0.05 g $ZnCl_2$, 0.05 g $MnCl_2$, 0.05 g $AlCl_3$, 0.05 g $NiCl_2$, 0.1 g $Na_2SeO_3.5H_2O$, 0.05 g $H_3BO_3$, 0.03 g $CuCl_2$, 0.05 g $(NH_4)_6Mo_7O_{24}.4H_2O$, 0.05 g $CoCl_2.6H_2O$, 0.5 g EDTA, 1.0 ml Conc. HCl, $H_2O$ to 1 l.

Flush and dispense 10 ml per bottle under $N_2/CO_2$ (4:1). Stopper with $O_2$-impermeable rubber stoppers and autoclave at 140° C. for 20 min. Add 0.1 ml DSM vitamin solution #141 from filter sterilized anaerobic solution and 0.2 ml of 2.5 g/l $Na_2S.9H_2O$ from autoclaved stock solution just before inoculation with sterile anaerobic syringe technique.

Cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol. 15 8:151–156).

Genomic Library Construction

Genomic DNA was partially digested with restriction enzyme Sau3A, and size-fractionated by electrophoresis on a 0.7% agarose gel. Fragments between 2 and 7 kb in size were isolated by electrophoresis onto DEAE-cellulose paper (Dretzen, G., Bellard, M., Sassone-Corsi, P., Chambon, P. (1981) A reliable method for the recovery of DNA fragments from agarose and acrylamide gels. Anal. Biochem., 112, 295–298).

Isolated DNA fragments were ligated to BamHI digested pSJ1678 plasmid DNA, and the ligation mixture was used to transform *E. coli* SJ2.

Cells were plated on LB agar plates containing 0.1% CMC (Sodium-Carboxy-Methyl-Cellulose, Aqualon, France) and 9 μg/ml Chloramphenicol to give 500–1000 c.f.u./plate and incubated overnight at 37° C.

Identification of Positive Clones by Activity

After inkubation the colonies were replica plated onto a set of LB+CAM agar plates and then further incubated at 37° C. for approx. 20 hours. An overlayer containing 0.1% CMC, 1% HSB agarose in an appropriate buffer pH 7 was poured onto the replica plates and incubated for approx. 20 hours at 65° C. Endoglucanase positive colonies were identified by staining with a 0.1% aqueous solution of Congo Red (SIGMA, USA) followed by washing in 2 M NaCl. Yellowish halos appeared at positions where endoglucanase positive clones were present.

Cells from enzyme-positive colonies were spread for single colony isolation on agar, and an enzyme-producing single colony was selected for each of the endoglucanase-producing colonies identified.

Characterization of Positive Clones

From the restreaking plates the endoglucanase positive clones were obtained as single colonies, and plasmids were extracted. Phenotypes were confirmed by retransformation of *E.coli* SJ2, and plasmids characterized by restriction digests.

Media

TY and LB agar (as described in Ausubel, F. M. et al. (eds.) "Current protocols in Molecular Biology". John Wiley and Sons, 1995).

Hybridization Conditions (to be used in Evaluating Property ii) of the DNA Construct of the Invention)

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 μg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity>1×10$^9$ cpm/μg) probe for 12 hours at ca. 45° C. The filter is then washed two times for 30 minutes in 2×SSC, 0.5% SDS at preferably not higher than 55° C., more preferably not higher than 60° C., more preferably not higher than 65° C., even more preferably not higher than 70° C., especially not higher than 75° C.

The nucleotide probe to be used in the hybridization is the endoglucanase encoding part of the DNA sequence obtainable from the plasmid present in *Escherichia coli* DSM 11201.

Immunological Cross-reactivity

Antibodies to be used in determining immunological cross-reactivity may be prepared by use of a purified endoglucanase. More specifically, antiserum against the endoglucanase of the invention may be raised by immunizing rabbits (or other rodents) according to the procedure described by N. Axelsen et al. in: *A Manual of Quantitative Immunoelectrophoresis*, Blackell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2). The following non-limiting examples illustrates the invention.

EXAMPLE 1

Cloning and Expression of an Endoglucanase from Dictyoglomus sp. DSM 6262

A library from Dictyoglomus sp., DSM 6262, was constructed in *E. coli* and screened as described in Materials and Methods. One positive transformant isolated was DSM 11201 containing the plasmid pSJ1678 comprising the DNA sequence encoding the cellulolytic enzyme of the invention.

The isolated *E. coli* clone was simultaneously tested on LB+CAM agar plates containing 0.1% AZCL beta-glucan, AZCL xyloglucan, AZCL HE cellulose, AZCL xylan, AZCL curdlan or AZCL galactomannan. The plates were incubated for approx. 48 hours at 37° C. followed by incubation at 65° C. Enzyme activity was identified by blue halos surrounding the colonies. The clone was found positive on AZCL beta-glucan, AZCL xyloglucan and AZCL HE cellulose.

Preparation of Enzyme Solution from the *E. coli* Clone DSM 11201

DSM 11201 was inoculated as a preculture in a shake flask containing 200 ml Super broth medium with the following composition (per liter): Tryptone 32 g, Yeast extract 20 g, NaCl 5 g, CMC 5 g, pH 7.2–7.3 adjusted with 1 M NaOH. Autoclaved 121° C., 20 minutes. After sterilisation added chloramphenicol to a final concentration of 6 mg/ml.

The shake flask was incubated on a rotary shaker at 280 rpm, 37° C., for 16 hours. 1 ml of the culture was inoculated to 100 shake flasks with 200 ml Super broth medium and incubated at 37° C., 280 rpm in 16 to 18 hours. Centrifugation at 3000 rpm of the 20 liter *E. coli* culture, resuspension of the pellet in 800 ml 50 mM Tris-maleat buffer, pH 7.0. The cells were ruptured at 800 bar with a Rannie High Pressure Laboratory Homogeniser. Centrifugation for 1 hour, 10.000 rpm and collection of the clear supernatant.

EXAMPLE 2

Purification and Characterization of the Endoglucanase Cloned from Dictyoglomus sp. DSM 6262

600 ml *E. coli* cell extract was first heat treated at 70° C. for 5 min followed by centrifugation at 5000 rpm for 20 min. The supernatant was filtrated through Whatman filter D and total 200 ml was obtained with an activity of 11 CMCU per ml (determination of CMCU, see below).

The solution was passed over a S-Sepharose column equilibrated with a 0.05 M sodium acetate buffer pH 5.0. The bound endoglucanase was eluted with 0.5 M sodium chloride and total a volume of 300 ml was obtained with 2 CMCU/ml. This solution was adjusted to pH 9.0 and equilibrated with 20 mM ethanolamine buffer pH 9.0 on an Amicon ultrafiltration cell with a membrane with a 10 kD cut off. Afterwards, when the conductivity is around 250 micro S/cm the solution is applied to a Q-Sepharose column equilibrated with the same buffer. The endoglucanase will bind and can be eluted using a sodium chloride gradient. Due to too high conductivity in the first trial we obtained only 2 ml with 65 CMCU/ml.

Finally, the solution was concentrated and applied to a size column Superdex 200 in 0.1 M sodium acetate pH 6.0 and the pure endoglucanase eluted in a volume of 22 ml which was concentrated using an Amicon ultrafiltration cell with a membrane with a 6 kD cut off. 1 ml with 40 CMCU per ml was obtained. This sample showed a single band in SDS-PAGE with a MW of 30 kD and a pI of 6.5. The protein was electroblotted and applied for N-terminal sequencing using an Applied Biosystems model 473A sequencer. The protein sequencer was run according to the manufacturer's instructions and the following sequence was obtained:
QTPKYKDAFILKAPSSGDVTTKNLPLTLELNFFNI AAY-(SEQ ID NO:3)

The pure endoglucanase has activity on p-Nitrophenyl-beta-D-cellobioside (Sigma), CMC, HE cellulose (Megazyme) and acid swollen cellulose.

One CMCU unit is defined as the amount of enzyme which release the equivalent to 1 mmol of glucose per min under standard conditions.

Standard Conditions: CMC Assay at 70° C.

The enzyme is incubated for 20 min. in a 0.75% CMC (7 L from Hercules) solution in a 0.1 M sodium barbiturate buffer pH 8.5. After incubation the increase in reducing end groups is determined using PHBAH (SIGMA H-988253H7704 (p-HYDROXY BENZOIC ACID HYDRAZIDE)) and with a glucose standard the formation of glucose equivalent end groups per min is calculated. (Lever, M. (1972) A new reaction for colometric determination of carbohydrates. Anal. Biochem. vol 47, page 273–279).

The endoglucanase showed 137 CMCU/mg og protein at 70° C. and pH 8.5 (50 CMCU per $A_{280}$).

Temperature Activity Profile of the Endoglucanase

The endoglucanase was incubated in the CMCU assay at pH 8.5 at different temperatures and the activity after 20 min. incubation was determined as described above. Incubations above 90° C. were not performed. The amount of reducing sugar obtained at this temperature was the highest and used for calculation of the relative activity at lower temperatures.

| Temp. | Rel. activity |
| --- | --- |
| 90° C. | 100% |
| 80° C. | 76% |
| 70° C. | 40% |
| 60° C. | 26% |
| 50° C. | 14% |
| 40° C. | 7% | pH Activity Profile

The endoglucanase was incubated in the CMCU assay at 70° C. using different buffers in the pH interval of 4.5 to 11 and the activity after 20 min. incubation was determined as described above.

Buffers: pH 4.5, 5.0 and 5.5; 0.1 M Na-acetate
pH 6.0; 0.1 M Na-MES
pH 6.5, 7.0 and 7.5; 0.1 M Na-MOPS
pH 8.0 and 8.5; 0.1 M EPPS
pH 9.0, 9.5, 10.0, 10.5 and 11.0; 0.1 M Na-glycine More than 50% relative activity was obtained in the interval of pH 5.5 to 11.

p-Nitrophenyl-beta-D-cellobioside Assay

A PNPU unit is defined as the amount of enzyme which release one mmole of p-Nitrophenol per minute from p-Nitrophenyl-beta-D-cellobioside (Sigma) under standard conditions.

Method: Steady state kinetic, direct detection of the product p-Nitrophenol, it gives a yellow color, which is detected at 405 nm. The activity is measured as the increase of absorbency, the linear part of the curve is used to determine the slope (AU/sec). The activity is calculated using an absorbance of p-Nitrophenol in phoshate buffer pH 7.5: Absorbance in 1 cm cuvette, 1 mM of 0.018 at 405 nm (0.014 at 420 nm).

Assay Conditions 475 ml 10 mM p-NP-beta-D-cellobioside in 0.1 M Na-phosphate buffer, pH 7.5 25 ml Enzyme solution.

Procedure

The measurement is made on HP 8452A Diode Array Spectrophotometer thermostatically controlled to 70° C. in a 0.75 ml cuvette, 1 cm width.

Absorbance at 405 nm is measured in 300 sec with a measurement every 20 sec.

The endoglucanase showed 170 PNPU per $A_{280}$ at 70° C. and pH 7.5.

Acid Swollen Cellulose

PASC stock solution was prepared the following way using ice cold acetone and phosphoric acid. 5 gram of cellulose (Avicel®) was moistered with water, and 150 ml ice cold 85% ortho-phosphoric acid was added. The mixture was placed in ice bath under slow stirring for 1 hr. Then 100 ml ice cold acetone was added with stirring. The slurry was transferred to a Buchner filter with pyrex sintered disc number 3 and then washed three times with 100 ml ice cold acetone, and sucked as dry as possible after each wash. Finally, the filter cake was washed twice with 500 ml water, sucked as dry as possible after each wash. The PASC was mixed with deionized water to a total volume of 300 ml, blended to homogeneity (using the Ultra Turrax Homogenizer) and stored in refrigerator (up to one month).

Substrate equilibration with buffer: 20 gram phosphoric acid swollen cellulose PASC stock solution was centrifuged for 20 min at 5000 rpm., the supernatant was poured of; the sediment was resuspended in 30 ml of buffer and centrifuged for 20 min. at 5000 rpm., the supernatant was poured of, and the sediment was resuspended in buffer to a total of 60 g corresponding to a substrate concentration of 5 g cellulose/liter. Buffer for pH 8.5 determination: 0.1 M Barbital.

Procedure

1. Dilution of Enzyme Samples

The enzyme solution is diluted in the same buffer as the substrate.

2. Enzyme Reaction

The substrate in buffer solution is preheated for 5 min. at 80° C. (2 ml).

Then the enzyme solution (diluted) 0,5 ml is added and mixed for 5 sec. Enzymes blanks are obtained by adding the stop reagent before enzyme solution. Incubate for 20 min. at 80° C. The reaction is stopped by adding 0.5 ml 2% NaOH solution and mixing for 5 sec.

The samples are centrifuged for 20 min. at 5000 rpm. 1 ml supernatant is mixed with 0.5 ml PHBAH reagent and boiled for 10 min. The test tubes are cooled in an ice water bath.

Determination of Reducing End Groups

The absorbancy at 410 nm is measured using a spectrophotometer. A standard glucose curve was obtained by using glucose concentrations of 5, 10, 15 and 25 mg/l in the same buffer and adding PHBAH reagent before boiling. The release of reducing glucose equivalent is calculated using this standard curve.

Determination of $k_{cat}$ and $K_m$

Catalytic activity on acid swollen cellulose was determined using the assay as described above under standard conditions at pH 8.5 and 80° C. with different substrate concentrations. The kinetic constants were calculated using the Michaëlis-Menten kinetic computer program Grafit. Based on the amino acid composition of the endoglucanase the molar extinction coefficient was determined to be 85630. Accordingly, the following data were obtained:

$k_{cat}$=77 per sec.

$K_m$=2.5 gram acid swollen cellulose per liter.

EXAMPLE 3

Expression of a Thermostable Endoglucanase in *Bacillus subtilis*

The *Bacillus subtilis* strain described below, harbouring the expression plasmid encoding the thermostable endoglucanase cloned from Dictyoglomus sp. DSM 6262, was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124

Braunschweig, Federal Republic of Germany, on Dec. 16, 1997 under the deposition number DSM 11903.

Materials

Strains

E. coli SJ2 (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321) Electrocompetent cells prepared and transformed using a Bio-Rad GenePulser™ as recommended by the manufacturer.

B.subtilis A164. This strain is a derivative of the B.subtilis ATCC 6051a, being sporulation deficient and having had the apr and npr genes disrupted. The disruptions were performed essentially as described in (Eds. A. L. Sonenshein, J. A. Hoch and Richard Losick (1993) Bacillus subtilis and other Gram-Positive Bacteria, American Society for microbiology, p.618). Competent cells were prepared and transformed as described by Yasbin, R. E., Wilson, G. A. and Young, F. E. (1975) Transformation and transfection in lysogenic strains of Bacillus subtilis: evidence for selective induction of prophage in competent cells. J. Bacteriol, 121:296–304.

Plasmids pUB110:. Plasmid described in (McKenzie,T., Hoshino, T., Tanaka,T. and Sueoka,N. The nucleotide sequence of pUB110: some salient features in relation to replication and its regulation Plasmid 15 (2), 93–103 (1986)) and (McKenzie,T., Hoshino,T., Tanaka,T. and Sueoka,N. Correction. A revision of the nucleotide sequence and functional map of pUB110 Plasmid 17 (1), 83–85 (1987)).

pMUTIN-4-MCS: Plasmid can be obtained from Laboratoire de Genetique Microbienne, Institut National de la Recherche Agronomique, 78352 Jouy en Josas—CEDEX, France.

Media

LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0.

AZCL-HE-cellulose is added to LBPG-agar to 1%. AZCL-HE-cellulose is from Megazyme, Australia.

BPX media is described in the international application published as WO 91/09129.

Methods

The plasmid was constructed and the clone was essentially established as follows:

The pMUTIN4MCS is an E.coli plasmid having a hybrid promoter SPAC (Yansura et al. (1984) Use of E.coli lac repressor and operator to control gene expression in Bacillus subtilis, PNAS, Vol81, pp. 439–443) and a lacZ gene under transcriptional control of this promoter. Furthermore the plasmid contains the laci gene under control of a Bacillus spe. penP Promoter. Thus when in B.subtilis the laci will be expressed and bind to the operator of the SPAC promoter-operator and this will inhibit transcription of the downstream sequence. The Promoter is the same as in Yansura et al., however the operator was modified into a perfect palindrome. A HindIII site just downstream of the Promoter-operator region made it possible to disrupt the lacZ gene by insertion of another gene, namely the endoglucanase gene of this invention. Thus leaving the expression of the endoglucanse under the control of the SPAC promoter-Operator.

In the E.coli plasmid pMUTIN4MCS a ribosome binding site (RBS) and a signal peptide with a SacII site for cloning purposes, were cloned as a HindIII-SacI fragment. Thus establishing the following ribosome binding site and signal peptide encoding DNA sequence: 1

HindIII (SEQ ID NO:4)
RBS
5'-AAGCTTGTTACACATTGAAAGGGGAGGAGAATCA*TGAAACAACAAAAA*

*CGGCTTTACGCCCGATTGCTGACGCTGTTATTTGCGCTCATCTTCTTGCTG*

NotI      SacI
*CCTCATTCTGCAGCCGCGGCA* GCGGCCGC GAGCTC-3'

Written in italic is the DNA sequence encoding a Bacillus sp. signal peptide which when fused to another DNA sequence encoding the mature part of a protein will direct this to the exterior of a Bacillus sp. cell.

The sequence above encodes the HindIII site of pMUTIN4MCS directly followed by a *Bacillus subtilis* RBS and a DNA sequence encoding a Bacillus spe. signal peptide ending with an artificially introduced SacII site which is followed by a NotI and a SacI restriction site. The plasmid was established in E.coli SJ2 by electroporation and plating on LB-agar plates with 100 µg/ml of ampicilin and incubating the cells overnight at 37° C. The resulting plasmid was termed pMUTIN4-Signal SacII-NotI.

The thermostable endoglucanase gene was cloned as a SacII-EagI digested PCR fragment.

The PCR fragment was obtained using the HiFi Expand PCR kit from Boehringer Mannheim and reaction was performed as recommended by the manufacturer. The DNA fragment was amplified from the plasmid pDSM11201. The thermostable endoglucanase gene was originally cloned from Dictyoglomus spe. DSM6262 and deposited as an E.coli clone (DSM 11201) harbouring a plasmid with the endoglucanase gene. The two PCR primers used were as follows:

30519
5'-CATTCTGCAGCCGCGGCACAAACTCCAA
AATACAAAGACGC-3' (SEQ ID NO:5)
30637
5'-CATGACACGGCCGATTATTTAAGCTCAAT
ATCAAAATTTGAG-3' (SEQ ID NO:6)

The PCR fragment and the pMUTIN4-Signal SacII-NotI were digested with SacII-EagI, ligated together and used to transform E.coli SJ2 by electroporation and plating on LB-agar plates with 100 µg/ml of ampicillin and incubating the cells overnight at 37° C. The resulting plasmid in SJ2 was termed pMB447A.

After having cloned the endoglucanase gene in fusion with the signal peptide from above (in the SacII-Not/EagI site) the following open reading frame resulted under the transcriptional control of the SPAC promoter-operator:

```
ATGAAACAACAAAAACGGCTTTACGCCCGATTGCTGACGCTGTTATTTGCGCTCATCTTCTTG    (SEQ ID NO:1)
CTGCCTCATTCTGCAGC
CGCGGCACAAACTCCAAAATACAAAGACGCATTTATACTTAAAGCACCTTCCTCAGGCGATGT
CACAACTAAAAATCTTC
CTCTCACCTTAGAACTCAACTTTTGGAATATTGCAAACTATGAAGGAAATACATGGATGGCAT
TTTATAAAGAAGAAGAT
ACTGTTGAATATTATGCCGACATAAAAAACATAGTACTTAAGGATAAAAATTCATGGGTACAT
GGATATCCTGAAGTCTA
CTATGGGTACAAACCATGGGCTGGCCATGGGAATTCCATTGAGAAATTAGCTCTTCCTAAAAA
GGTATCAGAATTTCCAG
ACGTTCTCTTCAATCTAAAATACAACATATGGTACGAGAAGAATCTTCCTATAAATTTTGCTA
TGGAAACATGGATAACA
AAAGAACCCTATCAGAAAACCGTTACTTCAGGGGATATAGAGATGATGGTATGGCTATATGCT
AATAGACTTTCTCCTGC
AGGGCGAAAGGTAGGAGAAGTAAAAATACCTATCATCCTAAACGGTAATCAAAAAGACATTAT
CTGGGAAGTATATCTTT
CCCCTATGAGCTGGGACTACGTGGCCTATAAATCAAAAGAAAATATTCTTCAAGGACAGGTAA
AAATACCAATAAATGAA
TTTTTGAAACACCTAAGAACAATTTTAGCCAACAATCCAAGTAGAATAACCCCAGAGAAATTT
GATCAGATGTATGTGAC
AGTCTGGGAAATTGGAACAGAATTTGGCGATCCATATACTACTGAGGCAAAATTTGGATGGAC
TTTCTCAAATTTTGATA
TTGAGCTTAAATAA
``` and the derived protein:

```
MKQQKRLYARLLTLLFALIFLLPHSAAAAQTPKYKDAFILKAPSSGDVTTKNLPLTLELNFWN    (SEQ ID NO:2)
IANYEGNTWMAFYKEED
TVEYYADIKNIVLKDKNSWVHGYPEVYYGYKPWAGHGNSIEKLALPKKVSEFPDVLFNLKYNI
WYEKNLPINFAMETWIT
KEPYQKTVTSGDIEMMVWLYANRLSPAGRKVGEVKIPIILNGNQKDIIWEVYLSPMSWDYVAY
KSKENILQGQVKIPINE
FLKHLRTILANNPSRITPEKFDQMYVTVWEIGTEFGDPYTTEAKFGWTFSNFDIELK.
```

0

In order to be able to propagate the pMB447A in *Bacillus subtilis* the *E.coli* plasmid was fused to a derivative of pUB110 (a plasmid propagateable in *B.subtilis*): In the NciI site of pUB110 a SacI and NotI site were introduced using a polylinker the resulting insert had the following sequence: CCCGGGAGCTCGCGGCCGCCCCGG(SEQ ID No:7)

The two NciI sites are underlined in-between these are the SacI and EagI (NotI) sites.

This plasmid was then SacI and EagI digested and ligated to SacI EagI digested pMB447A, the ligation was used to transform *Bacillus subtilis* A164. Clones were established and grown overnight on LBPG-10 Kana AZCL-HE-cellulose plates. Next day these plates were incubated at 70° C. for 5 hours and the appearance of blue haloes indicated positive expression of the thermostable endoglucanase.

When analysing the plasmid DNA isolated from the clone MB505 (DSM 11903) it was apparent that the plasmid had underwent recombination and the resulting plasmid was smaller than the expected plasmid size of 12.5 kb. Thus it appeared that the plasmid had lost most of the *E.coli* plasmid pMUTIN 4 Signal SacII-NotI, resulting in a plasmid of the approximate size of 5.5 kb.

The resulting plasmid had the following essential features:

The endoglucanase encoded on the plasmid of DSM 11903 was positively expressed without having to add IPTG and the plasmid conferred resistance to 10 μg/ml of Kanamycin.

The MB505 was cultivated 5 days in 500 ml shake-flasks with two baffles and 100 ml of BPX media at 37° C. at 300 rpm.

Purification and Characterization 5000 ml shake flask culture fluid from Bacillus with the clone MB 505 was received, and the culture fluid was heat treated by heating it to 70° C. and kept at this temperature for 5 min under stirring. It was then cooled down and centrifuged at 9000 rpm for 20 min. 4000 ml of clear supernatant was obtained containing 2.4 CMCU per ml.

The CMCU was determined at 70° C. and pH 8.5.

6000 CMCU was applied to 3000 ml DEAE A-50 Sephadex equilibrated in 50 mM Mes buffer pH 6.2. The nonbound material contained total 5700 CMCU.

The non bound material was applied to a 1000 ml Q-Spharose column equilibrated with 20 mM ethanolamin buffer pH 9.5. The bound enzyme was eluted using a NaCL gradient.

The partly purified product was concentrated using an amicon ultrafiltration cell with a membrane with a cut-off value of 6 kDa.

The concentrated fraction was formulated with 40% nonopropyleneglycol.

A total of 250 ml with a concentration of 9.7 CMCU per ml (2425 CMCU in total) was obtained and used for application trials.

Immunological Methods

Highly purified cellulase from Dictyoglomus (from example 2) was used for production of antiserum.

The immunization procedure was conducted at DAKO using rabbits. Each rabbit was immunized with 100 μl cellulase (0.4 mg protein per ml) mixed with 100 μl adjuvant. Each rabbit was immunized 15 times with one weeks interval. The rabbit serum was collected and the gamma-globulin purified from the serum.

Mancini plates, for example 25 ml 1% agarose gel (15*10 cm), with 50 µl gammaglobulin (A280=106.5) and with 4 mm well in which 10 µl sample was applied and incubated for 1 day at room temperature in a wet chamber.

The plate was washed in 0.95 NaCl water for several times and stained with coomassei blue following standard procedure.

The following diameters were obtained from either the highly purified Dictyoglomus cellulase or the partly purified MB505 formulated, respectively:

Highly Purified Dictyoglomus Cellulase

40 CMCU gave 11.5 mm in diameter.

20 CMCU gave 9.5 mm in diameter.

10 CMCU gave 7 mm in diameter

Formulated MB505

10 CMCU 8 mm in diameter.

Other family 12 cellulases (e.g. from the fungal genera Trichoderma, Humicola, Aspergillus) did not form immuno-precipitate under these conditions.

EXAMPLE 4

Biopolishing of Dictyoglomus Cellulase at 90° C.

Experimental

| Materials and equipment | |
|---|---|
| Apparatus: | Mathis Pad-steam Range, Type: PSA-HTF |
| Fabric: | Bleached interlock knitted cotton fabric (Test fabrics Inc.): N.O. white, 100% cotton, style 460. The fabric was cut into pieces of a size 20 x 30 cm (approx. 12.5 g each). |
| Enzyme: | Dictyoglomus, batch MB505, 9.7 CMC U/ml |
| Buffer: | 15 mM phosphate buffer pH 6.0 |
| | 15 mM phosphate buffer pH 8.1 |

Padding Procedure

Fabric swatches were conditioned in a standard AATCC (American Association of Textile Chemists and Colourists) climate room (65±2% relative humidity and 70±3° F. temperature) for at least 24 hours. Their weight was obtained.

Enzyme solutions were made from mixing enzyme with buffer. The pH was adjusted and the enzyme activity in solutions were shown in Table 1 below. Swatches were immersed in enzyme solutions for less than 45 seconds and then padded. After the padding, swatches were weighed and hung in the Mathis steamer immediately. The percentage of solution on fabric shown as wet pickup of fabric swatches was also presented in Table 1:

TABLE 1

| Fabric (#) | Enzyme Solution (CM CU/ml) | Solution pH | Wet pick-up (% w/w) |
|---|---|---|---|
| 1 | 0 | 6 | 125 |
| 2 | 0 | 8.1 | 128 |
| 3 | 4.8 | 6 | 130 |
| 4 | 4.8 | 8.1 | 131 |
| 5 | 9.7 | 6 | 137 |
| 6 | 9.7 | 8.1 | 137 |

Biopolishing in Steamer

Fabric swatches were treated in steamer at following conditions:

Temperature: 90° C.

Time: 90 min

Relative Humidity: 100%

All swatches are transferred and rinsed in de-ionized water for at least 5 minutes. They were air dried and then conditioned in the AATCC climate room for at least 24 hours before evaluation.

Evaluation

Strength Loss: Fabric strength was measured on Mullen Burst tester model C according to ASTM D3786–87. The data are average of at least 8 measurements.

Pilling note: Measured according to ASTM D 4970–89 using a Matindale Pilling Tester at 500 revolutions. Pilling on the fabric are evaluated visually from scale 1 to 5, where 1 is very severe pilling and 5 is no pilling. The data are average of at least 2 measurements.

Results and Conclusions

The results are summarized below and the data are shown in Table 2 and 3.

1. As enzyme concentration increases, pilling note increases (in table 3),
2. Dictyoglomus cellulase gives better pilling note at pH 8.1 than at pH 6.0 (Table 3),
3. At present conditions, Biopolishing gives little fabric strength loss at pH 6.0 (less than 5%), but no strength loss was detected at pH 8.1.

It can be concluded that biopolishing of cotton fabric with Dictyoglomus cellulase improve fabric pilling resistance significantly at conditions in this study. At preferred conditions such as pH about 8, good pilling resistance was obtained without detectable strength loss.

TABLE 2

| Fabric (#) | Strength Loss (%) | Pilling Note (500 rev) |
|---|---|---|
| 1 | 0 | 1.5 |
| 2 | 0 | 2 |
| 3 | 2.4 | 2 |
| 4 | 0 | 2.75 |
| 5 | 3.5 | 2.5 |
| 6 | 0 | 3 |

TABLE 3

| Cellulase (CMCU/g) | Pilling Note 500 rev, pH 6 | Pilling Note 500 rev, pH 8.1 |
|---|---|---|
| 0 | 1.5 | 2.0 |
| 4.8 | 2.0 | 2.8 |
| 9.7 | 2.5 | 3.0 |

We claim:

1. An enzyme having endoglucanase activity and optimum activity above 85° C., selected from one of:

(a) a polypeptide encoded by the DNA sequence of SEQ. ID NO:1;

(b) a polypeptide produced by culturing a cell comprising the sequence of SEQ. ID NO:1 under conditions wherein the DNA sequence is expressed;

(c) a polypeptide encoded by the endoglucanase encoding part of the DNA sequence obtainable from the plasmid in Esoherichia coli DSM 11201; or (d) an enzyme having a sequence of at least 60% identity to SEQ ID NO:2 when identity is determined by GAP provided in the GCG program package using a GAP creation penalty of 3.0 and GAP extensions penalty of 0.1.

2. The enzyme of claim 1 having endoglucanase activity and optimum activity above 90° C.

3. The enzyme of claim 1 having endoglucanase activity and optimum activity above 100° C.

4. The enzyme of claim 1, obtainable from Dictyoglomus wherein the enzyme of (d) exhibits an activity towards carboxymethycellulose (CMC assay) at 70° C. and pH 10 which is higher than 50% relative to the activity at 70° C. and optimum pH.

5. An enzyme having endoglucanase activity and optimum activity above 85° C. encoded by the DNA sequence of SEQ ID NO:1.

6. The enzyme of claim 5 produced by culturing a cell comprising the sequence of SEQ ID NO:1 under conditions wherein the DNA sequence is expressed.

7. An enzyme having endoglucanase activity and optimum activity above 85° C. encoded by the endoglucanase endcoding part of the DNA sequence obtainable from the plasmid in Escherichia coli DSM 11201.

8. An enzyme having endoglucanase activity and optimum activity above 85° having a sequence of at least 60% identity to SEQ ID NO:2 when identity is determined by GAP provided in the GCG program package using a GAP creation penalty of 3,0 and GAP extension penalty of 0.1

9. An isolated enzyme having endoglucanase activity, in which the enzyme is (i) free from homologous impurities, and (ii) produced by culturing a cell comprising the DNA sequence of SEQ ID NO:1 wherein the enzyme is produced and isolated.

10. An enzyme preparation comprising the enzyme of claim 9.

11. The preparation of claim 10, further comprising one or more enzymes selected from mannanases, galactanases, xylanases, arabinanases, pectin acetyl esterases, polygalacturonases, rhamnogalacturonases, pectin lyases, pectate lyases, pectin methylesterases, endoglucanases, proteases, lipases, amylases, cutinases, peroxidases, laccases, cellobiohydrolases and transglutaminases.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 867 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

```
ATGAAAAAAT CTTTACTTTC TCTTATCCTC ATACTTCTTC TTATTACTCT CTCCTTCAGT      60
CAAACTCCAA AATACAAAGA CGCATTTATA CTTAAAGCAC CTTCCTCAGG CGATGTCACA     120
ACTAAAAATC TTCCTCTCAC CTTAGAACTC AACTTTTGGA ATATTGCAAA CTATGAAGGA     180
AATACATGGA TGGCATTTTA TAAAGAAGAA GATACTGTTG AATATTATGC CGACATAAAA     240
AACATAGTAC TTAAGGATAA AAATTCATGG GTACATGGAT ATCCTGAAGT CTACTATGGG     300
TACAAACCAT GGGCTGGCCA TGGGAATTCC ATTGAGAAAT TAGCTCTTCC TAAAAAGGTA     360
TCAGAATTTC CAGACGTTCT CTTCAATCTA AAATACAACA TATGGTACGA AAGAATCTT     420
CCTATAAATT TTGCTATGGA AACATGGATA ACAAAAGAAC CCTATCAGAA AACCGTTACT     480
TCAGGGGATA TAGAGATGAT GGTATGGCTA TATGCTAATA GACTTTCTCC TGCAGGGCGA     540
AAGGTAGGAG AAGTAAAAAT ACCTATCATC CTAAACGGTA ATCAAAAGA CATTATCTGG     600
GAAGTATATC TTTCCCCTAT GAGCTGGGAC TACGTGGCCT ATAAATCAAA AGAAAATATT     660
CTTCAAGGAC AGGTAAAAAT ACCAATAAAT GAATTTTTGA AACACCTAAG AACAATTTTA     720
GCCAACAATC AAGTAGAAT AACCCCAGAG AAATTTGATC AGATGTATGT GACAGTCTGG     780
GAAATTGGAA CAGAATTTGG CGATCCATAT ACTACTGAGG CAAAATTTGG ATGGACTTTC     840
TCAAATTTTG ATATTGAGCT TAAATAA                                        867
```

(2) INFORMATION FOR SEQ ID NO: 2:

(i) SEQUENCE CHARACTERISTICS:
       (A) LENGTH: 288 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 2:

```
Met Lys Lys Ser Leu Leu Ser Leu Ile Leu Ile Leu Leu Leu Ile Thr
 1               5                  10                  15

Leu Ser Phe Ser Gln Thr Pro Lys Tyr Lys Asp Ala Phe Ile Leu Lys
            20                  25                  30

Ala Pro Ser Ser Gly Asp Val Thr Thr Lys Asn Leu Pro Leu Thr Leu
        35                  40                  45

Glu Leu Asn Phe Trp Asn Ile Ala Asn Tyr Glu Gly Asn Thr Trp Met
    50                  55                  60

Ala Phe Tyr Lys Glu Glu Asp Thr Val Glu Tyr Tyr Ala Asp Ile Lys
65                  70                  75                  80

Asn Ile Val Leu Lys Asp Lys Asn Ser Trp Val His Gly Tyr Pro Glu
```

```
                     85                  90                  95
Val Tyr Tyr Gly Tyr Lys Pro Trp Ala Gly His Gly Asn Ser Ile Glu
                100                 105                 110

Lys Leu Ala Leu Pro Lys Lys Val Ser Glu Phe Pro Asp Val Leu Phe
            115                 120                 125

Asn Leu Lys Tyr Asn Ile Trp Tyr Glu Lys Asn Leu Pro Ile Asn Phe
        130                 135                 140

Ala Met Glu Thr Trp Ile Thr Lys Glu Pro Tyr Gln Lys Thr Val Thr
145                 150                 155                 160

Ser Gly Asp Ile Glu Met Met Val Trp Leu Tyr Ala Asn Arg Leu Ser
                165                 170                 175

Pro Ala Gly Arg Lys Val Gly Glu Val Lys Ile Pro Ile Ile Leu Asn
            180                 185                 190

Gly Asn Gln Lys Asp Ile Ile Trp Glu Val Tyr Leu Ser Pro Met Ser
        195                 200                 205

Trp Asp Tyr Val Ala Tyr Lys Ser Lys Glu Asn Ile Leu Gln Gly Gln
    210                 215                 220

Val Lys Ile Pro Ile Asn Glu Phe Leu Lys His Leu Arg Thr Ile Leu
225                 230                 235                 240

Ala Asn Asn Pro Ser Arg Ile Thr Pro Glu Lys Phe Asp Gln Met Tyr
                245                 250                 255

Val Thr Val Trp Glu Ile Gly Thr Glu Phe Gly Asp Pro Tyr Thr Thr
            260                 265                 270

Glu Ala Lys Phe Gly Trp Thr Phe Ser Asn Phe Asp Ile Glu Leu Lys
        275                 280                 285

(2) INFORMATION FOR SEQ ID NO:3:

(i) SEQUENCE CHARACTERISTICS:
        (A) LENGTH: 38 amino acids
        (B) TYPE: amino acid
        (C) STRANDEDNESS: single
        (D) TOPOLOGY: linear (xi) SEQUENCE DESCRIPTION: SEQ ID NO:3:

Gln Thr Pro Lys Tyr Lys Asp Ala Phe Ile Leu Lys Ala Pro Ser Ser
1               5                  10                  15

Gly Asp Val Thr Thr Lys Asn Leu Pro Leu Thr Leu Glu Leu Asn Phe
            20                  25                  30

Phe Asn Ile Ala Ala Tyr
        35

(2) INFORMATION FOR SEQ ID NO:4:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO:4:

AAGCTTGTTA CACATTGAAA GGGGAGGAGA ATCATGAAAC AACAAAAACG GCTTTACGCC    60

CGATTGCTGA CGCTGTTATT TGCGCTCATC TTCTTGCTGC CTCATTCTGC AGCCGCGGCA   120

GCGGCCGCGA GCTC                                                    134

(2) INFORMATION FOR SEQ ID NO:5:

(i) SEQUENCE CHARACTERISTICS:
```

```
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:5:

CATTCTGCAG CCGCGGCACA AACTCCAAAA TACAAAGACG C                              41

(2) INFORMATION FOR SEQ ID NO:6:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:6:

CATGACACGG CCGATTATTT AAGCTCAATA TCAAAATTTG AG                             42

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:7:

CCCGGGAGCT CGCGGCCGCC CCGG                                                24
```